United States Patent [19]

Grundei

[11] Patent Number: 5,433,747
[45] Date of Patent: Jul. 18, 1995

[54] VOICE PROSTHESIS

[75] Inventor: Hans Grundei, Luebeck, Germany

[73] Assignee: Eska Medical GmbH & Co, Luebeck, Germany

[21] Appl. No.: 71,796

[22] Filed: Jun. 4, 1993

[30] Foreign Application Priority Data

Jun. 6, 1992 [DE] Germany .................. 42 18 739.7

[51] Int. Cl.⁶ .................................................. A61F 2/20
[52] U.S. Cl. ...................................... 623/9; 128/207.15
[58] Field of Search .................... 623/9, 12; 128/207.15

[56] References Cited

U.S. PATENT DOCUMENTS

| | | | |
|---|---|---|---|
| 4,040,428 | 8/1977 | Clifford | 623/9 |
| 4,439,872 | 4/1984 | Henly-Cohn et al. | 623/9 |
| 4,582,058 | 4/1986 | Depel et al. | 623/9 |
| 4,808,183 | 2/1989 | Panje | 623/9 |

Primary Examiner—Jerome L. Kruter
Attorney, Agent, or Firm—Panitch, Schwarze Jacobs & Nadel

[57] ABSTRACT

A voice prosthesis is provided for use in a shunt between the trachea and the esophagus of a laryngectomized patient. The voice prosthesis has a tube-shaped metal part (1) with a funnel-shaped expansion (2) that opens towards its tracheal end. Within the path of the stream of air from the trachea to the esophagus there is provided at least one element (3) that is caused to vibrate by the stream of air passing through the prosthesis, thereby producing an audible tone. With this prosthesis, a laryngectomized patient can produce a much more natural sounding voice than has previously been the case.

15 Claims, 2 Drawing Sheets

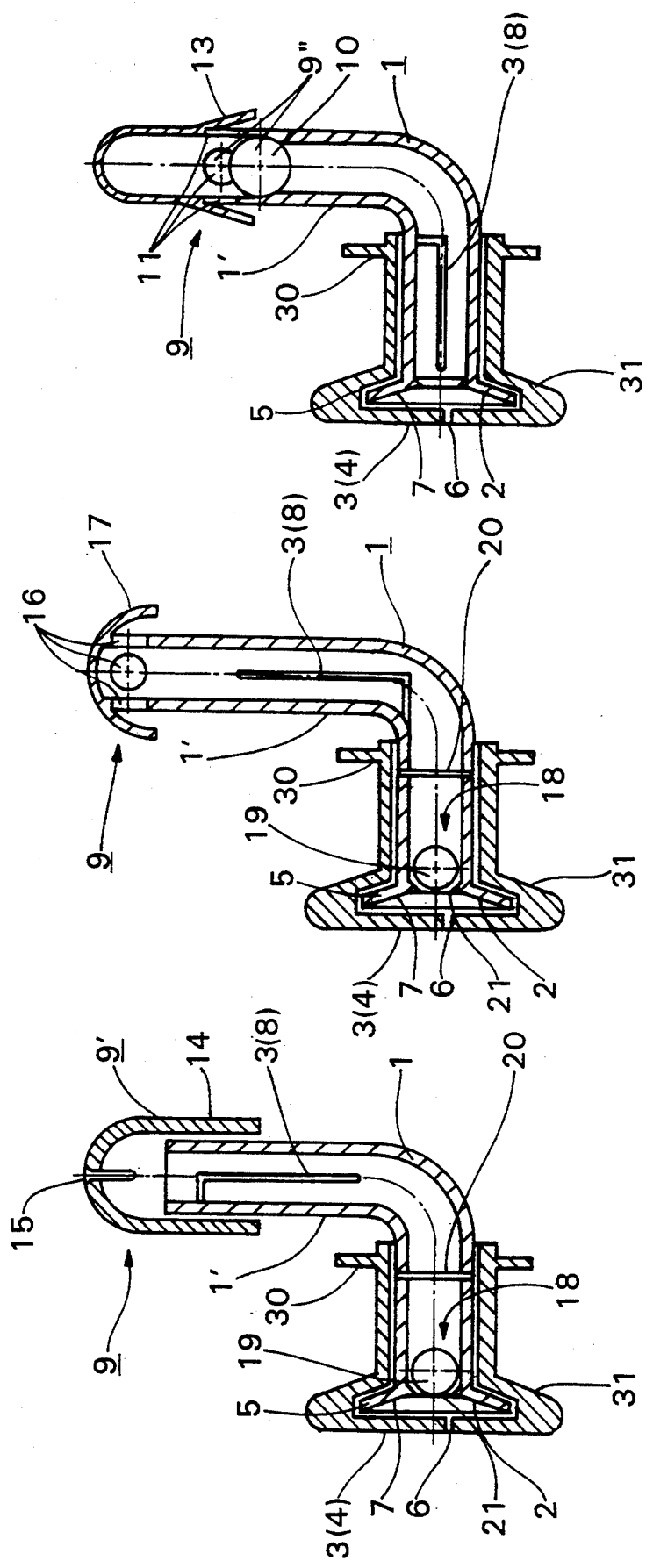

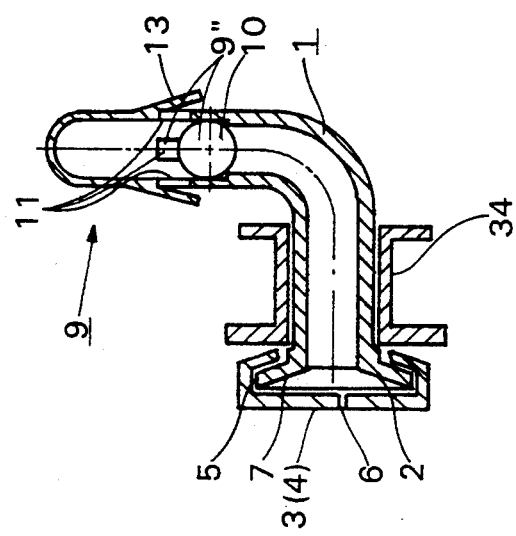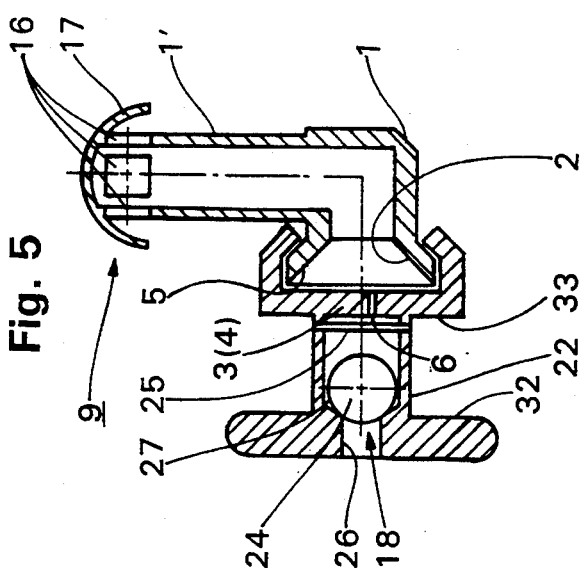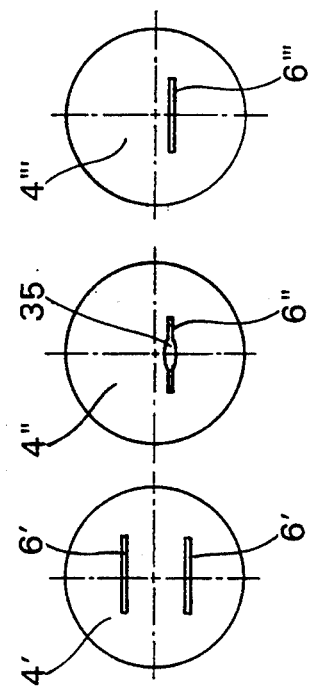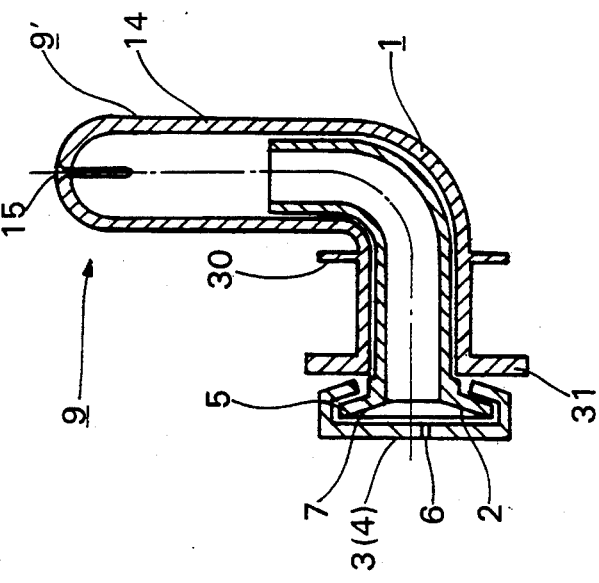

VOICE PROSTHESIS

FIELD OF THE INVENTION

The present invention concerns a voice prosthesis for laryngectomized patients, that is, for patients whose larynx has been surgically removed and who have therefore lost their natural voices.

BACKGROUND OF THE INVENTION

In the past, vocal rehabilitation of laryngectomies took place, for example, through learning of the so-called esophagus voice, for the creation of which the patient pressed air into his gullet (esophagus) and, through conscious relaxation of the pseudoglottis, was able to release the airstream which was then subject to articulation by his tongue and lips. Another possibility consisted of the use of so-called Servox devices, which were placed into the neck area and which vibrated. The vibration oscillations were subject to articulation through movement of the lips.

The acoustic pattern of the artificial voices produced in these ways does not correspond to a natural acoustic pattern in any way. Very deep and "raspy" artificial voices are produced. It is probably for this reason that use of these artificial voices, especially in female patients, is afflicted by an extremely high psychological inhibition threshold.

At the beginning of the 1980s, surgery could provide an improvement to the extent that a shunt could be inserted between the windpipe (trachea), which was otherwise surgically closed in the area of the pharynx, and the esophagus. So-called voice prostheses were placed into this shunt. The patient could breathe through this surgically created connection between the trachea and the environment through the so-called tracheastoma, which it was also necessary to create when using the earlier surgical techniques, and in more recent times, through the so-called tracheastoma valve, as it is described and claimed in EP-B-O 221 973, for example. If the patient now wanted to speak, he closed the tracheastoma with his finger or the valve closed automatically due to the higher air pressure, so that air could flow from the trachea through the shunt and into the esophagus.

A so-called voice prosthesis of this type is known from DD-275183 A1, for example. The designation of the one-way valve described therein as a voice prosthesis is certainly inappropriate. This valve does nothing except admit an air stream between the trachea and the esophagus, and prevent the entrance of food particles or saliva from the esophagus back into the trachea. The latter is of course extremely important, since otherwise complications such as pneumonia can occur. From a technical standpoint, however, the valve described in the cited reference merely closes off a different source of air when compared with the creation of the esophagus voice described earlier. The artificial voice created with the valve is also extremely deep in its frequency range, and is therefore very difficult to accept, especially for female patients.

DE-A-32 11 126 shows a so-called larynx prosthesis used in a shunt between the trachea and esophagus of a laryngectomized 10 patient, having an open, funnel-shaped expansion toward the tracheal end. This prosthesis does nothing except form a transition between trachea and esophagus, as has already been described in more detail. Similar prostheses are shown in U.S. Pat. No. 4,808,183, EP-A-O 279 484, and EP-A-O 222 509.

Another type of device is shown by DE-A-22 53 496 and JP-A-2-174843, for example. In these, devices are provided that have an extracorporeal tone-generating element in order to make use of an artificially generated frequency for speech modulation. The arrangement as an extracorporeal device is of course very burdensome for the patients, partly because these devices are visible to everyone with whom the patient converses.

Against this background, it is the object of the present invention to provide a voice prosthesis for use in the shunt between the trachea and esophagus of a laryngectomized patient, with which prosthesis the frequency range of the artificial voice can be adapted to the frequency range of the natural voice, and all parts of which can be implanted intracorporeally.

SUMMARY OF THE INVENTION

The above objects are achieved by the voice prosthesis of the present invention according to which a voice prosthesis comprising a tube-shaped metal part that exhibits an open, funnel-shaped expansion towards the tracheal end is provided with at least one element within the path of airstream from the trachea to the esophagus, which element can be caused to vibrate and thereby produce an audible tone by the air that enters by way of the prosthesis.

In contrast to the conventional so-called voice prostheses that are—as already explained—nothing more than a one-way valve, the invented voice prosthesis comprises an element that can vibrate at a preset frequency. This element causes vibrations to occur in the air column inside the voice prosthesis, which are then transmitted into the esophagus and pharyngeal area of the patient. The articulation of words then takes place through lip movements. Through use of an element that is capable of vibration, it is possible to preset a specific voice range for each individual patient through appropriate selection of the vibrating element. Thus, one would select for a female patient a vibrating element that generates a higher tone than an element that would be used for male patients.

As with a conventional shunt valve, the invented voice prosthesis remains in situ for approximately eight weeks. At that point, deposits and the occurrence of fungus (candida) make it necessary to exchange and clean the prosthesis. Basically, however, this does not present a problem. To do this, the voice prosthesis is removed through the tracheastoma just as a conventional shunt valve, and a new or cleaned voice prosthesis is inserted through the tracheastoma back into the shunt between the trachea and the esophagus.

The voice prosthesis remains in situ because the tube-shaped metal part has, in known fashion, two ring-shaped flanges made of silicone, for example. The walls of the esophagus and trachea, which may be sewn together, are placed between these flanges.

In accordance with a first embodiment of the voice prosthesis, the tone-generating element is a flexible membrane that covers the funnel-shaped expansion. This membrane reaches behind the rim of the funnel-shaped expansion, and exhibits at least one slit in the area of the expansion that is covered by the membrane.

When the tracheastoma is closed, air is directed against the flexible membrane which is thereby caused to vibrate. The slit (at least one) in the membrane produces a tone in the same way, visually speaking, as the pressed together lips of a trumpet player. The fact that the membrane reaches behind the rim of the funnel-shaped expansion provides an exceptionally stable seating of the membrane, while at the same time making it possible for the remaining parts to vibrate freely.

Preferably, the funnel-shaped expansion is dimensioned in such a way that the membrane does not contact the base of the expansion, even during maximum amplitude vibrations. This insures that the artificial voice never simply "fades away", even if there is a large stream of air and consequent high pressure on the membrane.

Advantageously, this membrane is made of silicone rubber with a Shore hardness in the 30 to 70 range. A high Shore hardness results in a relatively high vibration frequency, while a low Shore hardness results in a relatively low frequency. Through selection of the membrane material, the voice prosthesis can be individually tailored to each patient. As a rule, female patients will thus receive a membrane with a high Shore hardness, male patients one with a relatively low Shore hardness.

In accordance with another embodiment of the invented voice prosthesis, the tone-generating element is a metallic voice plate located in the open lumen of the tube-shaped metal part and anchored in its wall. The voice plate has basically an L shape, whereby the short leg serves for mounting, while the long leg carries out the intended vibrations. The voice prosthesis in accordance with this embodiment can be tailored very exactly with regard to the vibration frequency it produces, namely through selection of the appropriate voice plate. The vibration frequency of the voice plate depends primarily on the width of its vibrating leg, the thickness of its material, and its length. These parameters can be tuned very exactly. Each patient can thus be given a voice prosthesis that makes available a vibration frequency individually selected by that patient.

With the invented voice prosthesis, special attention must be given to making sure that no food particles or saliva can enter, since it cannot otherwise perform its function. In accordance with an advantageous modification, all embodiments of the voice prosthesis may have, at least at the esophageal end, a protective device that prevents the entry of food particles and saliva.

In accordance with a first embodiment, the tube-shaped metal part of the voice prosthesis can be closed at the esophageal end by a one-way valve. Preferably, the valve is formed inside the tube-shaped metal part by a movable ball and openings in the side wall of the tube-shaped metal part, whereby the ball is movable between a location that gives access to the entrance to the funnel-shaped expansion, and a location that closes it. When the patient begins speaking, he deliberately directs a larger stream of air through the invented voice prosthesis. The increased air flow pushes the above-mentioned ball forward to the extent that the openings are unobstructed so that air can go out through them and into the esophagus.

The protective function can be further increased by means of protective flaps covering the openings in the side walls to protect against entry of foreign objects into the trachea. These flaps can be made of elastomeric silicone and can be bonded to the tube-shaped metal part above the openings. The protective flaps shield the openings like a protective roof.

In accordance with another embodiment, the one-way valve at the esophageal end is a flutter valve formed by pushing over the tube-shaped metal part a plastic tube that is closed at the esophageal end except for a longitudinal slit. When the patient begins to speak, the increased air flow spreads the plastic tube slightly in the area of the longitudinal slit so that air can exit from the voice prosthesis. At the end of the speaking process, the longitudinal slit closes by itself due to the material's inherent resilient forces.

In accordance with another embodiment, the protective device at the esophageal end is not a one-way valve. Instead, provision can be made that the esophageal end of the tube-shaped metal part of the voice prosthesis is closed at its front end, and that at least one opening is provided in the side walls in this area. This is covered by a protective hood that redirects the air flow coming out of the side opening.

In accordance with an advantageous modification, in addition to the protective device at the esophageal end, a further protective device in the form of a one-way ball valve is placed at the tracheal end. This measure substantially increases the protection against contamination of the interior of the voice prosthesis, thereby effectively preventing damage to the vibration element membrane or the voice plate. A positive side effect of the additional tracheal end ball valve can be seen in that because of this arrangement, the patient can increasingly breathe through the pharyngeal space instead of through the tracheastoma.

In a concrete construction, the tracheal end protective device can be formed in such a way that in the interior of the tube-shaped metal part in the tracheal end region, a freely moving ball is installed that is limited in its movement away from the funnel-shaped expansion, that is in the direction of the esophagus, by a limit stop positioned across the diameter of the tube-shaped metal part, and is limited in its movement in the direction of the funnel-shaped expansion by a ball valve seat formed in this expansion. The limit stop positioned across the tube-shaped metal part can be a metal plate or a wire, for example. Preferably, it should offer only slight resistance to the flow of air through the voice prosthesis. When the patient begins to speak, the ball is pressed against the above-mentioned limit stop, and a flow of air through the voice prosthesis is made possible. In contrast, during breathing in through the tracheastoma the ball is sucked into the ball valve seat at the back end of the funnel-shaped expansion due to the low air pressure that then prevails at the air entry opening of the voice prosthesis.

A further embodiment of the voice prosthesis with an additional trachea-end protective device in the form of a one-way valve is configured in such a way that the trachea-end protective device is constructed as a longitudinal tube-shaped capping piece that is pushed onto the funnel-shaped expansion, grips the funnel-shaped expansion from the back, and houses in its interior the freely moving ball of a one-way ball valve. This ball is limited in its movement in the direction of the funnel-shaped expansion by a limit stop stretching across the diameter of its lumen, and in its movement in the direction of the air entry opening by a ball valve seat formed in the interior of this capping piece. The limit stop, as well as the ball valve seat, is constructed in principle in the same manner as in the previously described embodiment. In an advantageous manner, the ring-shaped flanges which have already been mentioned, between which the sewn together esophagus and trachea walls lie, are formed on the tube-shaped capping piece. Preferably, the capping piece is formed of silicone.

The voice prosthesis in accordance with the invention is advantageously formed in something of an L shape so that after insertion of the voice prosthesis into the shunt between the trachea and esophagus, the esophageal end points towards the cranium, that is upwards.

BRIEF DESCRIPTION OF THE DRAWINGS

The foregoing summary of the invention, as well as the following detailed description of preferred embodiments, will be better understood when read in conjunction with the appended drawings. For the purpose of illustrating the invention, there are shown in the drawings embodiments which are presently preferred, it being understood, however, that the invention is not limited to the specific arrangements and instrumentalities disclosed.

FIG. 1 is a cross-sectional plan view of a first embodiment of a voice prosthesis according to the present invention;

FIG. 2 is a cross-sectional plan view of a second embodiment of a voice prosthesis according to the present invention;

FIG. 3 is a cross-sectional plan view of a third embodiment of a voice prosthesis according to the present invention;

FIG. 4 is a cross-sectional plan view of a fourth embodiment of a voice prosthesis according to the present invention;

FIG. 5 is a cross-sectional plan view of a fifth embodiment of a voice prosthesis according to the present invention;

FIG. 6 is a cross-sectional plan view of a sixth embodiment of a voice prosthesis according to the present invention; and FIGS. 7a–7c are top views of the various embodiments of the membrane.

In the drawing Figures, the corresponding parts have been provided with the same reference numbers.

DETAILED DESCRIPTION OF THE PREFERRED EMBODIMENTS

FIG. 1 shows a first embodiment of the voice prosthesis in accordance with the invention. The main part of the voice prosthesis is the tube-shaped metal part 1, here bent into an L shape. At its end lying next to the tracheal end when in situ, the metal part exhibits an open, funnel-shaped expansion 2. This open, funnel-shaped expansion 2 is, in the embodiment shown, covered by an element 3 that produces an audible tone when air is blown against it, or in the present case, by a membrane 4. This membrane 4 grips the rim 5 of the funnel-shaped expansion 2 from the back. In this way, an exceptionally stable locating of the membrane 4 over the funnel-shaped expansion 2 is achieved. In the embodiment shown, the back side of the membrane is formed with more of a hose-shaped extension, and has at its distal end a ring-shaped flange 30. Between this flange 30 and the back side 31 of the funnel-shaped expansion 2, the walls of the trachea and the esophagus (not shown, but possibly sewn together) come together in a sealing position.

The membrane part including the membrane 4 with its hose-shaped extension and the protruding flange 30 is made of silicone rubber. The Shore hardness of this material lies in the range of about 30 to 70. A higher Shore hardness allows the membrane 4 to generate a higher tone, a lower Shore hardness a lower tone, when the membrane has air blown against it from the trachea. For tone generation, there is placed in membrane 4 at least one slit 6 through which air can flow into the tube-shaped metal part 1. The funnel-shaped expansion 2 is dimensioned in such a way that the membrane 4 does not touch the floor 7 of the expansion 2, even when the membrane vibrates with maximum oscillation amplitude.

In addition, the voice prosthesis represented in FIG. 1 has an additional element 3 that can vibrate and produce an audible tone, namely a metal voice plate 8 anchored in the free lumen of the tube-shaped metal part 1. This voice plate 8 is configured in almost an L shape, with a long leg that can vibrate in the lumen of the metal part 1, and with a short leg that is anchored in the wall 1' of the metal part 1, for example in a slot that has been provided therein.

At the esophageal end, the voice prosthesis is provided with a protective device 9 that prevents food particles and saliva from entering the voice prosthesis. In the present case, the tube-shaped metal part 1 is provided with a one-way valve 9', which comprises a plastic tube 14 that is pushed over the tube-shaped metal part 1. It lies close to the wall 1' of the tube-shaped metal part 1; this cannot be seen clearly in FIG. 1 due to representation limitations. This plastic tube has a longitudinal slit 15 in its esophageal end. When air flows from the trachea to the esophagus, the longitudinal slit spreads and allows air to flow into the pharyngeal area of the patient. If the air flow is interrupted, for instance when the patient stops speaking, the longitudinal slit closes due to the material's inherent resilient forces, and effectively prevents the entry of food particles or saliva into the voice prosthesis.

The represented voice prosthesis also has as an additional protective means on the tracheal end, a protective device in the form of a one-way ball valve 18. This valve comprises a ball 19 positioned in the tube-shaped metal part 1 in such a way that it can move freely between a limit stop 20 and a valve seat 21. This limit stop 20 can be a metal strip or wire seated in the wall 1' of the tube-shaped metal part 1. In either case, it offers only slight resistance to the flow of air.

The limit stop 20 limits the movement of the ball 19 in the direction away from the funnel-shaped expansion 2. In the mouth area of the open lumen of the tube-shaped metal part 1, in the funnel-shaped expansion 2, a valve seat is formed that prevents any further movement towards the left of the drawing. When the patient begins to speak, the ball 19 is forced from the represented position at the valve seat 21 towards the limit stop 20, and air can flow through the tube-shaped metal part 1, causing the membrane 4 and the voice plate 8 to vibrate, and, as the slit 15 of the flutter valve opens, flow from the trachea into the esophagus. The vibrations arriving at the pharyngeal area are then subject to articulation by the patient.

FIG. 2 shows a second embodiment. At this point, note should be taken of the differences versus the voice prosthesis shown in FIG. 1. The anchoring location for the voice plate 8 is different from that shown in FIG. 1. Basically, the anchoring location for the voice plate is unimportant. What is relevant, however, is that the long, vibrating leg have enough room to carry out maximum amplitude vibrations.

Primarily, it is the protective device 9 on the esophageal end that most differs from what is shown in FIG. 1. Here, the tube-shaped metal part 1 is closed at its front opening. In its place, side openings 16 are provided in the side wall 1'; these openings are protected against the entry of food particles and saliva by an overhanging protective hood 17. The protective hood 17 can be an integral component of the tube-shaped metal part 1. However, it can also be made of silicone and be bonded to the metal part 1.

In FIG. 3 an embodiment is shown that, in contrast to those of FIGS. 1 and 2, has no additional protective device on the tracheal end. Instead, the voice plate 8 is anchored at this location. The protective device 9 on the esophageal end also differs from the embodiments explained above. Here, the tube-shaped metal part 1 is again closed at the esophageal end. Openings 11 in the side wall 1' are provided as air entry openings. A ball 10 of a one-way valve 9" is situated in the interior of the tube-shaped metal part 1. The arrangement is such that when the patient begins to speak, the ball 10 is lifted by the flow of air to the extent that a passage is opened between the funnel-shaped expansion 2 and the openings 11. The openings 11 are shielded by protective flaps 13 that are made of an elastic material and are bonded, for example, to the metal part 1 above the openings 11.

FIG. 4 illustrates another embodiment, which only has available a single element 3 that can vibrate and produce an audible tone, namely via the membrane 4 which grips the rim 5 of the funnel-shaped expansion 2 from behind. Here, as protective device 9 on the esophageal end, a one-way valve 9' is provided, which is formed from a plastic tube 14 that is pushed over the tube-shaped metal part 1 and that has—as already shown in FIG. 1—a longitudinal slit 15. The manners of functioning are the same.

In contrast to the embodiment of FIG. 1, the plastic tube 14 is lengthened and has as integral components flanges 30 and 31, between which the tracheal and esophageal walls (not shown) come together in a sealing position.

FIG. 5 shows a further embodiment of the voice prosthesis. The tube-shaped metal part 1 again forms the main part, with a protective device 9 at the esophageal end that has already been explained by means of the embodiment in FIG. 2. As the tone-generating element 3, a membrane 4 is used that grips the rim 5 of the funnel-shaped expansion 2 of the tube-shaped metal part 1 from behind and covers the funnel-shaped expansion. The membrane 4 is an integral component of a long, narrow, tube-shaped capping piece 22, which in its tube-shaped section contains a one-way ball valve 18 as an additional protective device on the tracheal end. The movable ball 24, that is a part of this valve, is limited in its movement towards the funnel-shaped expansion 2 by a limit stop 25 that crosses the tube section. This limit stop is formed like limit stop 20, as explained by means of FIGS. 1 and 2. The ball 24 is limited in its movement towards the air entry opening 26 by a ball valve seat 27, which is formed in the air entry opening 26 in the mouth area of the lumen of the tube section. The trachea and esophagus walls (not shown) are brought together between sections 32 and 33, which act as flanges.

FIG. 6 shows a final embodiment, again with a tone-generating element 3, namely a membrane 4 that is stretched over the funnel-shaped expansion 2 and grips the expansion's rim from behind. The protective device 9 and one-way valve 9" on the esophageal end correspond with the ones already described by means of FIG.3. In contrast with the previously described embodiments, in the present case a sleeve-like tube piece 34, preferably made of silicone, is pushed over the tube-shaped metal part 1 up to the funnel-shaped expansion 2. Part 34 has without more specific designation, the flanges between which the trachea and esophagus walls (not shown) are placed.

Finally, three views of membranes 4', 4", and 4'" are shown in FIG. 7. Membrane 4' as shown in FIG. 7a has two slits 6' The membrane 4" shown in 7b has only one slit 6", which has in its center a hole-like expansion 35. Membrane 4'" as shown in FIG. 7c has instead only one slit 6'". Various parameters such as the pitch of the tone can be adjusted by varying the numbers and/or arrangements of slits.

The present invention may be embodied in other specific forms without departing from the spirit or essential attributes thereof and, accordingly, reference should be made to the appended claims, rather than to the foregoing specification as indicating the scope of the invention.

I claim:

1. Voice prosthesis for use in a shunt between the trachea and esophagus of a laryngectomized patient, comprising a tube-shaped part (1) having a tracheal end and an esophageal end and forming at least part of a passageway for flow of air form the trachea to the esophagus, said part having an open, funnel-shaped expansion (2) towards the tracheal end thereof, and at least one audible tone generating element (3) situated in a path of the air flow from the trachea to the esophagus, said element generating an audible tone when caused to vibrate by the air flow passing through the tube-shaped part.

2. Voice prosthesis according to claim 1 wherein said audible tone generating element comprises a flexible membrane (4, 4', 4", 4'") that covers the funnel-shaped expansion (2), said membrane gripping a rim (5) of the funnel-shaped expansion (2) from behind and having at least one slit (6, 6', 6", 6'") in the area where the membrane covers the expansion (2).

3. Voice prosthesis according to claim 2 wherein the membrane (4, 4', 4", 4'") comprises silcone rubber with a Shore hardness in the range of about 30 to 70.

4. Voice prosthesis according to claim 1 wherein the funnel-shaped expansion (2) is so dimensioned that the membrane (4, 4', 4", 4'") does not touch the base (7) of the expansion (2), even in a case of maximum-amplitude vibrations of the membrane.

5. Voice prosthesis according to claim 1 wherein said audible tone generating element comprises a metal voice plate (8) that is situated in an open lumen of and anchored in a wall of the tube-shaped part (1).

6. Voice prosthesis according to claim 1, further comprises a protective device (9) which protects the tube-shaped part from entry of food particles and saliva, at least on the esophageal end.

7. Voice prosthesis according to claim 6 wherein the tube-shaped part (1) can be closed on the esophageal end by a one-way valve (9', 9").

8. Voice prosthesis according to claim 7 wherein the valve is formed interiorly of the tube-shaped part (1) by a movable ball (10) and openings (11) in a side wall (1') of the tube-shaped part (1) and wherein the ball (10) is movable between a position that opens access to the funnel-shaped expansion (2) and a position that closes said access.

9. Voice prosthesis according to claim 8 wherein the openings (11) in the side wall (1') of the tube-shaped part (1) are provided with protective flaps (13) which protect against entry of foreign objects into the trachea.

10. Voice prosthesis according to claim 6, wherein the tube-shaped part (1) is closed at its front opening at the esophageal end, and wherein a side wall (1') at the esophageal end has a side opening (16), which is covered by a protective hood (17) that deflects the air flow existing from the side opening (16).

11. Voice prosthesis according to claim 7, wherein the valve is a flutter valve, formed from a plastic tube (14) pushed over the tube-shaped part (1), said tube being closed at the esophageal end except for a longitudinal slit (15) therein.

12. Voice prosthesis according to claim 6 further comprising an additional protective device provided at the tracheal end, said additional protective device comprising a one-way ball valve (18).

13. Voice prosthesis according to claim 12 wherein said ball valve comprises a ball (19) positioned interiorly of the tube-shaped part (1) in an area of the tracheal end, said ball being limited in its movement in a direction away from the funnel-shaped expansion (2) by a limit stop (20) extending across a diameter of the tube-shaped part (1), and limited in its movement in a direction toward the funnel-shaped expansion by a ball valve seat (21) formed in said expansion.

14. Voice prosthesis according to claim 12, wherein the additional protective device comprises a long, narrow tube-shaped capping piece (22) that is pushed over the funnel-shaped expansion and grips the funnel-shaped expansion (2) from behind, and said one-way ball valve (18) comprises a ball (24) positioned in a freely movable manner, said ball being limited in its movement towards the funnel-shaped expansion (2) by a limit stop (25) that extends across a lumen of the expansion, and being limited in its movement towards an air entry opening (26) by a ball valve seat (27) formed interiorly of the tube-shaped capping piece.

15. Voice prosthesis according to claim 1, wherein the tube-shaped part is made of metal.

* * * * *